US012799524B2

(12) United States Patent
Hu et al.

(10) Patent No.: US 12,799,524 B2
(45) Date of Patent: *Nov. 17, 2026

(54) CRISPR-BASED ASSAY FOR DETECTING TB IN BODILY FLUIDS

(71) Applicant: The Administrators of the Tulane Educational Fund, New Orleans, LA (US)

(72) Inventors: Tony Ye Hu, New Orleans, LA (US); Bo Ning, New Orleans, LA (US); Zhen Huang, New Orleans, LA (US)

(73) Assignee: The Administrators of the Tulane Educational Fund, New Orleans, LA (US)

(*) Notice: Subject to any disclaimer, the term of this patent is extended or adjusted under 35 U.S.C. 154(b) by 641 days.

This patent is subject to a terminal disclaimer.

(21) Appl. No.: 18/162,652

(22) Filed: Jan. 31, 2023

(65) Prior Publication Data

US 2024/0043911 A1 Feb. 8, 2024

Related U.S. Application Data

(63) Continuation-in-part of application No. 17/797,425, filed as application No. PCT/US2021/016931 on Feb. 5, 2021.

(60) Provisional application No. 62/971,210, filed on Feb. 6, 2020.

(51) Int. Cl.
*C12Q 1/6823* (2018.01)
*C12Q 1/6832* (2018.01)
*C12Q 1/689* (2018.01)

(52) U.S. Cl.
CPC ......... *C12Q 1/6823* (2013.01); *C12Q 1/6832* (2013.01); *C12Q 1/689* (2013.01)

(58) Field of Classification Search
CPC .... C12Q 1/689; C12Q 1/686; C12N 15/1003; C12N 2310/20; A61P 37/08; A61K 39/35; C07K 14/35
See application file for complete search history.

(56) References Cited

U.S. PATENT DOCUMENTS

| | | | |
|---|---|---|---|
| 2014/0113305 A1 | 4/2014 | Schorey | |
| 2016/0115471 A1 | 4/2016 | Kim et al. | |
| 2017/0247747 A1 | 8/2017 | Allard et al. | |

FOREIGN PATENT DOCUMENTS

| | | | | |
|---|---|---|---|---|
| CN | 109811072 | | * | 5/2019 |
| CN | 109811072 | A | * | 5/2019 |
| CN | 110541022 | A | | 11/2022 |
| JP | 2004536596 | 1 | | 12/2004 |
| JP | 2017530710 | A | | 10/2017 |
| RU | 2163638 | C1 | | 2/2001 |
| WO | 2002101353 | A2 | | 12/2002 |
| WO | 2016057905 | A1 | | 4/2016 |
| WO | 2017207825 | A1 | | 12/2017 |
| WO | WO-2018001884 | A1 | * | 1/2018 ............. C12N 15/01 |
| WO | 2018170340 | A1 | | 9/2018 |
| WO | 2019104058 | A1 | | 11/2018 |
| WO | 02101353 | A3 | | 12/2022 |

OTHER PUBLICATIONS

Extended European Search report for Application EP21750130 dated Mar. 13, 2024.

Shell, S. S.; Prestwich, E. G.; Baek, S-H.; Shah, R. R.; Sassetti, C. M.; Dedon, P. C.; Fortune, S. M. "DNA methylation impacts gene expression and ensure hypoxic survival of *Mycobacterium tuberculosis*." (2013) PLOS Pathogens, vol. 9, Issue 7, e1003419.

Invitrogen AccuPrimeTM Pfx DNA Polymerase—Product Information Sheet.

Ai, J-W.; Zhou, X.; Xu, T.; Yang, M.; Chen, Y.; He, G-Q.; Pan, N.; Cai, Y.; Li, Y.; Wang, X.; Su, H.; Wang, T.; Zeng, W.; Zhang, W-H. "CRISPR-based rapid and ultra-sensitive diagnostic test for *Mycobacterium tuberculosis*." (2019) Emerging Microbes & Infections, vol. 8, pp. 1361-1369.

Office Action for Japanese application No. 2022-547848 dated Apr. 30, 2025.

"Notice of Reasons for Refusal" dated Jan. 27, 2026, issued by the Japan Patent Office regarding corresponding application No. 2022-547848.

International Preliminary Report on Patentability—IPRP)—PCT/US2021/016931.

Vietnamese Office Action received for Application No. 1-2022-05681.

Office Action Received in JP Application No. 2022547848.

Jing-Wen Ai, et al."CRISPR-based rapid and ultra-sensitive diagnostic test for *Mycobacterium tuberculosis*" Emerging Microbes & Infections, 8 (1) , 1361-1369, 2019.

Shell, Scarlet S. "DNA Methylation Impacts Gene Expression and Ensures Hypoxic Survival of *Mycobacterium tuberculosis*" PLOS Pathog (2013), 9 (7): e1003419.

AccuPrime Pfc DNA Polymerase Product Information Sheet May 2016.

(Continued)

*Primary Examiner* — Cynthia B Wilder
(74) *Attorney, Agent, or Firm* — Thomas | Horstemeyer, LLP

(57) ABSTRACT

The present disclosure describes a method for detecting the presence of *Mycobacterium tuberculosis* in a bodily fluid sample. The method utilizes CRISPR effector proteins along with a guide RNA and a reporter molecule, such that when the guide RNA hybridizes with a target nucleotide fragment, the CRISPR effector protein cleaves the reporter molecule, resulting in a detectable signal.

17 Claims, 4 Drawing Sheets

Specification includes a Sequence Listing.

(56) References Cited

OTHER PUBLICATIONS

Fernandez-Carballo, et al. "Toward the Development of Circulating Free DNA-Based In Vitro Diagnostic Test for Infectious Diseases: a Review of Evidence for Tuberculosis." Journal of Clinical Microbiology. 2019, 57 (4):e01234-18.

* cited by examiner

CRISPR-BASED ASSAY FOR DETECTING TB IN BODILY FLUIDS

PRIOR RELATED APPLICATIONS

The application is a continuation-in-part of U.S. Ser. No. 17/797,425, filed Aug. 3, 2022, which is a 371 application of PCT/US21/16931, filed Feb. 5, 2021, which claims priority to U.S. Ser. No. 62/971,210, filed Feb. 6, 2020. Each of these applications is incorporated by reference herein in its entirety for all purposes.

FEDERALLY SPONSORED RESEARCH STATEMENT

Not applicable.

FIELD OF THE DISCLOSURE

The disclosure generally relates to a method of detecting tuberculosis (TB) in circulating fluids, such as serum, plasma, urine and cerebrospinal fluid (CSF), and more particularly relates to a method of detecting tuberculosis in serum using CRISPR-based reporter system.

BACKGROUND OF THE DISCLOSURE

Tuberculosis (TB) is a serious disease that affects millions of people each year, and is among the top 10 causes of death worldwide. Delay in diagnosis can lead to death. While sputum samples are primarily used to diagnose pulmonary TB, some patients are not able to expectorate sputum, for example those that are very sick or very young.

Currently TB diagnosis relies on Xpert MTB/RIF®, which requires a sputum sample. Although the bacteria load is high in sputum, it can be difficult to collect as a sample. Additionally, sputum may not be collected from every TB patient, especially for extrapulmonary TB patients, and extrapulmonary TB (EPTB) is common, especially in HIV patients.

Blood is an alternative candidate for TB detection, especially in HIV-infected patients, for it is easier and more reliable to collect than sputum. However, *Mycobacterium tuberculosis* is rarely detected by blood test. TB blood culture could take several weeks to become positive and requires facilities with certain equipment. Nucleic acid amplification tests are less than ideal with blood due to low sensitivity (20-55%), possibly because of the low bacteria load, the presence of PCR inhibitors or small volume of samples typically employed for these tests.

Therefore, there is the need for a highly sensitive serum test for tuberculosis that has high specificity.

SUMMARY OF THE DISCLOSURE

The present disclosure describes a method for detecting *Mycobacterium tuberculosis* ("MTB") as well as non-tuberulous *mycobacterium* (NTM) in a serum sample. Examples of NTM includes but not limited to: *M. kansasii, M. simiae, M. marinum, M. scrofulaceum, M. szulgai, M. avium* complex (MAC), *M. ulcerans, M. xenopi, M. malmoense, M. terrae, M. haemophilum, M. genavense, M. chelonae, M. abscessus, M. fortuitum, M peregrinum, M smegmatis* and *M. flavescens*. Please refer to FIG. 1, which illustrates the method of this disclosure. In the first step, nucleic acids are extracted from the sample, such as a serum sample. The nucleic acid is then amplified targeting an MTB-specific sequence, if present. The product of amplification is then reacted with a gRNA-CRISPR system along with a reporter molecule. If the MTB-specific sequence is present, the gRNA will hybridize with it to activate the CRISPR effector protein, which then cleave the reporter molecule and one can determine the presence of MTB based on measurement of signals produced by the reporter molecule.

CRISPR (Clustered Regularly Interspaced Short Palindromic Repeats) is a family of DNA sequences found within the genomes of prokaryotic organisms such as bacteria and archaea. These sequences are derived from DNA fragments of bacteriophages that have previously infected the prokaryote and are used to detect and destroy DNA from similar phages during subsequent infections, and therefore they serve as an important part of the prokaryotes' immune system.

CRISPR-associated protein 9 ("Cas9") is an enzyme that uses CRISPR sequences as a guide to recognize and cleave specific strands of DNA that are complementary to the CRISPR sequence. The Cas9 endonuclease is a four-component system that includes two small crRNA molecules and trans-activating CRISPR RNA (tracrRNA). The two RNA sequences were fused into a single guide RNA (gRNA), which guides Cas9 to find and cut the DNA target specified by the guide RNA. Cas9 enzymes together with CRISPR sequences form the basis of a technology known as CRISPR-Cas9 that can be used to edit genes within organisms. By manipulating the nucleotide sequence of the guide RNA, the artificial Cas9 system could be programmed to target any DNA sequence for cleavage.

Nuclease Cas12a (formerly known as Cpf1), another member of the Cas family, showed several key differences from Cas9 including: causing a 'staggered' cut in double stranded DNA as opposed to the 'blunt' cut produced by Cas9, relying on a 'T rich' protospacer adjacent motifs, thus providing alternative targeting sites to Cas9, and requiring only one CRISPR RNA for successful targeting.

Cas13 (including four subtypes: Cas13a-d) functions similarly to Cas9, using a ~64-nt guide RNA to encode target specificity. The Cas13 protein complexes with the guide RNA via recognition of a short hairpin in the crRNA, and target specificity is encoded by a 28 to 30-nt spacer that is complementary to the target region. In addition to programmable RNase activity, all Cas13s exhibit collateral activity after recognition and cleavage of a target transcript, leading to non-specific degradation of any nearby transcripts regardless of complementarity to the spacer.

In one embodiment, the CRISPR effector protein is Cas12a (formerly known as Cpf1), Cas9 or Cas13. However, other CRISPR effector proteins can be used, as long as effective detection with high specificity can be achieved.

By properly designing the gRNA by varying its length and location in a particular gene, one can thus target a DNA fragment with the desirable specificity and sensitivity. Therefore, with the CRISPR-Cas-gRNA method of this disclosure, highly sensitive and specific detection of MTB in serum can be achieved in a matter of hours. It is expected to be able to detect a single copy of MTB DNA in a 5 µl of serum sample.

The method can also be used to distinguish MTB and nontuberculous mycobacteria (NTM), and identify *Mycobacterium* species by targeting species-specific DNA fragments. NTM infection has similar symptoms to those produced by MTB, while over 150 different species of NTM have been described, the identification of these organisms in pulmonary specimens does not always equate with active infection. Supportive radiographic and clinical findings are needed to establish the diagnosis, and treating or eradicating NTM infections has been challenging.

Further variation can be carried out in order to enhance MTB detection. In one embodiment, the DNA extracted from the serum sample can be further enriched by first treated with anti-DNA antibodies. In another embodiment, the DNA extracted from the serum sample can be further treated with anti-human DNA antibodies in order to deplete human DNA from the sample.

In one embodiment, anti-human DNA antibody is anti-5-methylcytidine (5 mC) antibody. However, other antibodies or proteins can be used, as long as it can bind to methylated DNA, such as anti-CpG DNA methylation, include 5-methylcytidine (5-mC) 5-hydroxymethyl-(5-hmC), 5-formyl-(5-fC) and 5-carboxy-(5-caC) cytosine antibodies; CpG DNA methylation binding proteins, methyl-CpG binding domain (MBD) proteins: MeCP2, MBD1, MBD2, MBD3, MBD4, MBD5, MBD6, TET1, TET2, TET3, Kaiso and their antibodies; as well as methylated RNA, such as anti-N7-methylguanosine (m7G), 5-methylcytidine (5 mC) and its oxidized form 5-hydroxylmethylcytidine (5hmC), N6-methyladenosine (m6A), N1-methyladenosine (m1A), pseudouridine (Ψ) and inosine (I) RNA antibodies; and methyl-RNA binding proteins METTL3, METTL14, FTO, ALKBH5, YTHDF1, YTHDF2, YTHDC1, ZNF217 and their antibodies.

Additionally, an anti-methylation DNA antibody may be used to deplete human DNA in the sample, in order to enrich pathogen-specific DNAs. This is especially applicable to enrich small size cfDNA.

The method of this disclosure can also be used to detect other pathogens in bodily fluid. The suitable pathogens may include but are not limited to: Respiratory syncytial virus (RSV), Cytomegalovirus (CMV), Varicella-zoster virus (VZV), Ebola virus, Marburg virus, West Nile virus (WNV), Zika virus, yellow fever virus, Herpes simplex virus (HSV), Monkeypox virus, Lyme diseases (bacterium *Borrelia burgdorferi* and *Borrelia mayonii*), malaria (*Plasmodium falciparum* and *Plasmodium vivax*), *Pneumocystis* pneumonia (*Pneumocystis jirovecii*), Human Herpesvirus (HHV).

Further enrichment can be achieved by isolating extracellular vesicles (EVs) prior to amplification. EVs are small membranous vesicles originating from the endosomal cell compartment when multi-vesicular bodies fuse with the plasma membrane. Secreted EVs are relatively stable and act as effective carriers of proteins, polypeptides, genes, soluble factors and membrane-bound receptors/ligands from a parent cell/bacterium, and therefore EVs isolated by ultracentrifuge from human serum or plasma can increase MTB DNA or RNA yield.

To isolate EVs, ultracentrifugation of greater than 100,000 g (42,000 rpm) is generally practiced. However, a person skilled in the art would appreciate other methods to isolate EVs, such as density-gradient separation, polymer-based precipitation, immunological selection, microfluidic isolation, size exclusion chromatography, membrane filtration, membrane affinity isolation.

Additional steps during cfDNA isolation may help increase the yield. For example, in the sample collection, serum or plasma is suggested to be processed less than 24 hours after blood draw, and the whole blood can be directed used for CRISPR test, wherein blood collection tube can be EDTA-K or Dk green Sodium heparin (Na tube).

The blocker protein (rTth and Tli) of PCR/RPA inhibitory components (IgG, hemoglobin, lactoferrin, etc.) may be added during blood sample processing, such that more amplification can be done for target sequences. Accessory proteins in PCR/RPA buffer (BSA, DNA hybridization, enhancers, and single-stranded DNA binding protein gp32) may also be added to further improve DNA amplification.

A protein digestion step may be added into sample processing to release further cfDNA. For example, the addition of proteinase K may be added to the sample processing buffer. Proteinase K can be used to digest protein and remove contamination from preparations of nucleic acid. Addition of Proteinase K to nucleic acid preparations rapidly inactivates nucleases that might otherwise degrade the DNA or RNA during purification, thereby increasing the yield of cfDNA.

When the amount of blood sample is large, a sample concentration column may be used to increase the concentration of DNAs.

Density-gradient separation refers to a method of loading samples onto sucrose solutions of different density profiles followed by ultracentrifugation, such that the EVs can be separated from protein aggregates and other impurities. For example, density gradient ultracentrifugation can be performed by loading plasma sample onto 50, 30, and 10% iodixanol layers and then centrifuged at 120,000×g for 24 hours. Ten fractions (F1-10) are collected from top to bottom, in which the ones with highest EVs content can then be further purified.

Polymer-based precipitation includes mixing the biological sample with polymer-containing precipitation solution, followed by incubation and centrifugation at low speed. One of the most common polymers used is polyethylene glycol.

Immuno-selection techniques use antibody-based separation methods targeting known surface markers on extracellular vesicles. Some of these markers include the well characterized tetraspanins (CD9, CD63, CD81) or immune-regulator molecules (MIC I&II) on the surface of the vesicles.

Microfluid isolation are based on trapping EVs in micro channels, and can be an option for low volume input of biofluids.

Size-exclusion chromatography is used to separate macromolecules on the base of size, not molecular weight. The technique applies a column packed with porous polymeric beads containing multiple pores and tunnels. The molecules pass through the beads depending on their diameter. It takes a longer time for molecules with small radii to migrate through pores of the column, while macromolecules elute earlier from the column. Size-exclusion chromatography allows precise separation of large and small molecules. Moreover, different eluting solutions can be applied to this method.

Membrane filtration can also be used for isolation of exosomes. Depending on the size of microvesicles, this method allows the separation of EVs from proteins and other macromolecules. EVs may also be isolated by trapping them via a porous structure. In particular, a micropillar porous silicon ciliated structure was designed to isolate 40-100 nm EVs. In addition to the standard filtration techniques, tangential flow filtration can also be used for effective isolation of EVs. This method is used for isolation of EVs with well-determined size by removing free peptides and other small compounds.

Various DNA amplification techniques can be used, as each technique has its advantages and disadvantages. The method of this disclosure can employ the common DNA amplification techniques, such as PCR, RPA, RCA, LAMP, etc., as well as any newly developed amplification methods.

The methods combine amplification and CRISPR detection. In amplification steps, hybridization enhancer component in reaction buffer can be used to enhance specific primer-template hybridization during every cycle of DNA amplification, preventing mispriming and improving DNA amplification specificity and yield. We expect to be able to amplify MTB DNA from a single copy in 5 µl of serum sample for CRISPR detection.

Hybridization enhancers can be further carried over to the CRISPR detection step, as they can further improve hybridization between of guide RNA and target sequences and reduce mismatch. Such enhancers are expected to be able to stabilize and enhance activities of CRISPR proteins and amplify signal.

In one embodiment, the hybridization enhancers are the thermostable AccuPrime accessory proteins. These enhance specific primer-template hybridization during every cycle of PCR, preventing mispriming and improving PCR specificity and yield. Other hybridization enhancers can also be used, as long as they can enhance specificity of hybridization. Non-limiting examples of hybridization enhancers include anionic polymers, in situ hybridization buffers and similar buffer components, AccuPrime accessory proteins, ULTRA-hyb™ Ultrasensitive Hybridization Buffer and the like.

As used herein, "CRISPR proteins" or "CRISPR effector protein" or "CRISPR enzymes" refers to Class 2 CRISPR effector proteins including but not limited to Cas9, Cas12a (formerly known as Cpf1), Csn2, Cas4, C2c1, Cc3, Cas13a, Cas13b, Cas13c, Cas13d. In one embodiment, the CRISPR effector proteins described herein are preferably Cpf1 effector proteins.

The CRISPR effector proteins may include but are not limited to: as, AsCas12a, FnCas12a, LbCas12a, AacCas12b, LwaCas13a, AapCas12b, UnlCas14a1/UN1Cas12f1, BbCas12a, HkCas12a, OsCas12a, BoCas12a, TsCas12a. AsCas12a refers to the Cas12a nuclease derived from Acidaminococcus sp. FnCas12a refers to the Cas12a nuclease derived from *Francisella novicida* U112. LbCas12a refers to the Cas12a nuclease derived from Lachnospiraceae bacterium. AacCas12b refers to the nuclease derived from *Alicyclobacillus acidoterrestris*. LwaCas13a refers to Cas13a protein derived from Leptotrichia *wadei*. AapCas12b refers to Cas12b protein derived from *Alicyclobacillus acidiphilus*. Un1Cas14a1 (or Un1Cas12f1) refers to the nuclease derived from uncultured archaeon. BbCa12a refers to the nuclease derived from Bacteroidales bacterium. HkCas12a refers to Cas12a nuclease derived from *Helcococcus kunzii*. OsCas12a refers to Cas12a nuclease derived from *Oribacterium* sp. BoCas12a refers to Cas12a nuclease derived from Bacteroidetes oral taxon 274. TsCas12a refers to Cas12a nuclease derived from *Thiomicrospira* sp.

As used herein, "guide RNA" or "gRNA" refers to the non-coding RNA sequence that binds to the complementary target DNA sequence to guide the CRISPR-Cas system in close contact with the target DNA strand.

As used herein, a "reporter molecule" refers to a single-stranded DNA or single-stranded RNA that is labeled with fluorescence and quencher, gold nanoparticles or biotin-FAM, and the dissociation of the reporter can be detected by either a fluorescence reader or colorimetric change in e.g., a paper lateral flow assay or spectrometer, and the like.

As used herein, the "target DNA fragment" is a portion of a MTB-specific DNA sequence. For example, IS6110 is an MTB complex-specific insertion sequence that is present in multiple copies per MTB genome. gryB mutation at positions 495, 516 and 533 have been reported to occur in fluoroquinolone-resistant MTB, and esxB is a CFT-10 protein secreted by MTB that contributes to the virulence thereof. Therefore, targeting these DNA fragments would facilitate the detection of MTB. Additional target DNA fragment can also be selected from the following MTB genes: rpoB, katG, inhA, rpsL, rrs, gyrA, gyrB, embB, eis and pncA.

As used herein, "DNA amplification" or "nucleic acid amplification" refers to natural and artificial processes by which the number of copies of a gene or a fragment of DNA is increased without a proportional increase in other genes.

As used herein, "polymerase chain reaction" or "PCR" refers to a method of amplifying a specific target region of a DNA strand by using a DNA polymerase and two primers (forward and reverse) that are complimentary to each end of the target region, along with dNTPs.

As used herein, "recombinase polymerase amplification" or RPA refers to a method of amplifying a specific target region using a recombinase, a single-stranded DNA-binding protein and strand-displacing polymerase. The recombinase pairs oligonucleotide primers with homologous sequence in duplex DNA, and the single-stranded DNA-binding protein binds to replaced strands of DNA to prevent the primers from being displaced. An optimal temperature at 37-42° C., the reaction progresses rapidly and results in specific DNA amplification without the need for thermal or chemical melting required by PCR.

As used herein, "nucleic acid sequence-based amplification" or NASBA refers to a primer-dependent method for continuously amplifying nucleic acids, particularly RNA sequences, in a single mixture at one temperature. Three enzymes are used: a reverse transcriptase, a RNase H, and T7 RNA polymerase. Two primers are used: the first primer includes a 3'-terminal sequence that is complementary to a target sequence and a 5'-terminal sense sequence of a promoter that is recognized by the T7 RNA polymerase; and the second primer includes a sequence complementary to the P1-primed DNA strand. First, an RNA template is given to the reaction mixture, where the first primer attaches to its complementary site at the 3' end of the template. The reverse transcriptase synthesizes the opposite, complementary DNA strand, extending the 3' end of the primer, moving upstream along the RNA template. At this time, RNAse H destroys the RNA template from the DNA-RNA compound (RNAse H only destroys RNA in RNA-DNA hybrids, but not single-stranded RNA). The second primer then attaches to the 5' end of the (antisense) DNA strand. Afterwards, the reverse transcriptase again synthesizes another DNA strand from the attached primer resulting in double stranded DNA, when the T7 RNA polymerase binds to the promoter region on the double strand. Since T7 RNA polymerase can only transcribe in the 3' to 5' direction, the sense DNA is transcribed and an anti-sense RNA is produced. This is repeated, and the polymerase continuously produces complementary RNA strands of the template which results in amplification.

Now a cyclic phase can begin similar to the previous steps. Here, however, the second primer first binds to the (−)RNA, and the reverse transcriptase now produces a (+)cDNA/(−)RNA duplex. RNAse H again degrades the RNA and the first primer binds to the now single stranded+ (cDNA), followed by the reverse transcriptase producing the complementary (−)DNA and creating a dsDNA duplex. Lastly, the T7 polymerase binds to the promoter region, produces (−)RNA, and the cycle is complete.

As used herein, "rolling circle amplification" or RCA refers to an isothermal enzymatic process where a short DNA or RNA primer is amplified to form a long single stranded DNA or RNA using a circular DNA template and special DNA or RNA polymerases. The RCA product is a concatemer containing tens to hundreds of tandem repeats that are complementary to the circular template.

As used herein, "loop-mediated isothermal amplification" or LAMP refers to a single tube DNA amplification method, where the target sequence is amplified at a constant temperature of 60-65° C. using either two or three sets of primers and a polymerase with high strand displacement activity in addition to a replication activity. Typically, 4 different primers are used to amplify 6 distinct regions on the target gene, which increases specificity. An additional pair of "loop primers" can further accelerate the reaction.

As used here, "reporter molecule" refers to a molecule having nucleotides linked to a detectable reporter group, such that when the nucleotides hybridize with a matching sequence, the reporter group produces detectable signals. Non-limiting reporter molecule includes a single-stranded DNA or RNA labeled with fluorescence and quencher, gold nanoparticles, biotin-FAM.

As used herein, "anti-human DNA antibodies" refers to anti-nuclear antibodies that target double stranded human DNA as antigen.

As used herein, "anti-MTB antibodies" refers to antibodies that target *Mycobacterium tuberculosis* DNA due to its specific methylation pattern.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBRE-VIATION | TERM |
|---|---|
| CRISPR | Clustered regularly interspaced short palindromic repeats |
| gRNA | Guide RNA |
| LAMP | Loop-mediated isothermal amplification |
| MTB | *Mycobacterium tuberculosis* |
| NASBA | Nucleic acid sequence-based amplification |
| PAM | Protospacer adjacent motif |
| PCR | Polymerase chain reaction |
| RCA | Rolling circle amplification |
| EV | Extracellular vesicle |
| NTM | Non-tuberculosis mycobacteria |

DETAILED DESCRIPTION

Figure 1:
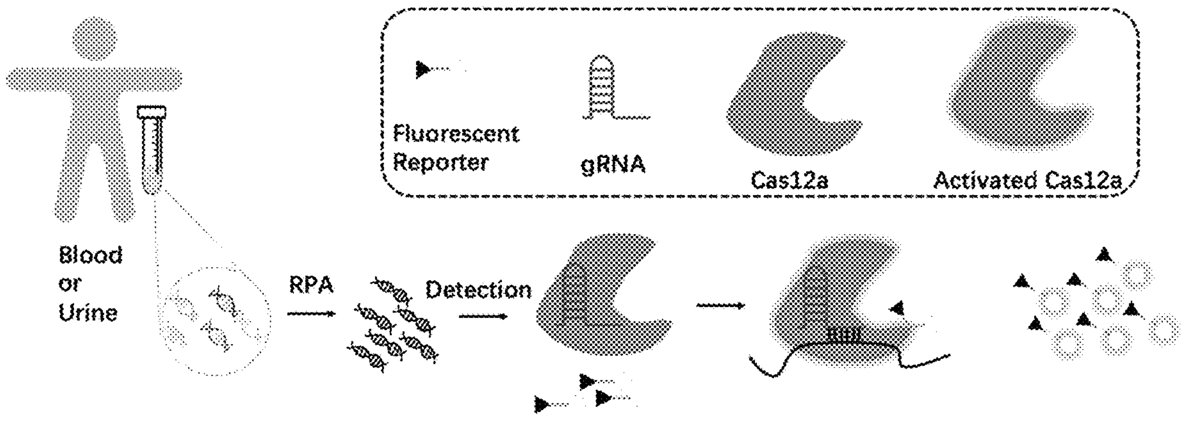
FIG. 1. Illustration of the method of this disclosure.

The disclosure provides novel method of detecting MTB DNA in a serum sample. The method comprises the steps of: a) extracting nucleic acids from a serum sample; b) amplifying a target nucleic acid sequence, and c) detecting presence of the target nucleic acid sequence using a CRISPR-mediated system, wherein the CRISPR-mediated system comprises a CRISPR effector protein, a guide RNA that hybridizes with the target nucleic acid sequence, and a reporter molecule.

Primers used in the DNA amplification step are designed to amplify only the MTB gene sequences that are conserved across *Mycobacterium* species or have been reported for certain drug resistance. For example, IS6110 is an MTB-specific insertion sequence. Other MTB-specific genes, such as those related to drug resistance, can also be amplified, such as esxB, rpoB, katG, inhA, rpsL, rrs, gyrA, gyrB, embB, eis and pncA.

The DNA sequence of *M. tuberculosis* IS6110 can be found at Accession Number X17348.1. The DNA sequence of *M. tuberculosis* esxB from strain H37Rv can be found at AL123456.3 (4352274-4352576). The DNA sequence of *M. tuberculosis* gryB from strain H37Rv can be found at AL123456.3 (5240-7267). In designing the primers, the focus is on amplifying the PAM recognizable by the CRISPR effector protein.

The gRNA sequences were designed in accordance with the target fragments and the primers used in the DNA amplification step. In other words, the gRNA sequences are portions of the IS6110, IS986, esxB, gryB, rpoB, katG, inhA, rpsL, rrs, gyrA, gyrB, embB, eis or pncA. These genes are listed in Table 1.

TABLE 1

| Candidate gene information for TB detection | | | |
|---|---|---|---|
| No. | Target Gene | Function | Reference |
| 1 | IS6110 | IS6110 is an insertion element of the *M. tuberculosis* complex | ncbi.nlm.nih.gov/nuccore/X17348.1?report=fasta |
| 2 | IS986 | IS986 belongs to the IS3-like family of insertion sequences of *M. tuberculosis* | ncbi.nlm.nih.gov/pmc/articles/PMC268102/ |
| 3 | exsB | Coding gene of ESAT-6 and CFP-10 | ncbi.nlm.nih.gov/gene?Db=gene&Cmd=ShowDetailView&TermToSearch=886194&itool=EntrezSystem2.PEntrez.Gene.Gene_ResultsPanel.Gene_RVDocSum |
| 4 | rpoB | Rifampin resistance relates gene of *M. tuberculosis* | ncbi.nlm.nih.gov/pubmed/8031050 |
| 5 | katG | Isoniazid resistance relates gene of *M. tuberculosis* | ncbi.nlm.nih.gov/pmc/articles/PMC500838/ |
| 6 | inhA | Isoniazid and ethionamide resistance relate gene of *M. tuberculosis* | ncbi.nlm.nih.gov/pubmed/8284673 |
| 7 | rpsL | Streptomycin resistance relates gene of *M. tuberculosis* | ncbi.nlm.nih.gov/pubmed/7968530 |
| 8 | rrs | Streptomycin and Kanamycin resistance relate gene of *M. tuberculosis* | ncbi.nlm.nih.gov/pmc/articles/PMC88513/ |
| 9 | gry A | Fluoroquinolone resistance relates gene of *M. tuberculosis* | ncbi.nlm.nih.gov/pubmed/22552454 |
| 10 | gryB | Fluoroquinolone resistance relates gene of *M. tuberculosis* | ncbi.nlm.nih.gov/pubmed/22552454 |
| 11 | embB | Ethambutol resistance relates gene of *M. tuberculosis* | aac.asm.org/content/53/3/1061 |
| 12 | eis | Kanamycin resistance relates gene of *M. tuberculosis* | ncbi.nlm.nih.gov/pubmed/22593564 |
| 13 | pncA | Pyrazinamide resistance relates gene of *M. tuberculosis* | ncbi.nlm.nih.gov/pmc/articles/PMC2346646/ |

The present invention is exemplified with respect to IS6110, esxB, gryB as the target fragment. However, these targets are exemplary only, and the invention can be broadly applied to other conserved regions among *Mycobacterium* species. The following examples are intended to be illustrative only, and not unduly limit the scope of the appended claims.

Example 1

Four samples were collected/prepared as follows. The method of this disclosure was performed on all four samples.

| Sample No. | Information | TB Status |
|---|---|---|
| 1 | Healthy human serum spiked with 100 copies of IS6110/esxB/gryB fragments | Positive |
| 2 | Healthy human serum spiked 10 ng of genomic DNA of MTB-H37RV | Positive |
| 3 | Healthy human serum 1 | Negative |
| 4 | Healthy human serum 2 | Negative |
| 5 | Healthy human serum 3 | Negative |
| 6 | Healthy human serum 4 | Negative |
| 7 | Healthy human serum 5 | Negative |
| 8 | Healthy human serum 6 | Negative |
| 9 | Healthy human serum 7 | Negative |
| 10 | Clinical TB-positive sample 1 | Positive |
| 11 | Clinical TB-positive sample 2 | Positive |
| 12 | Clinical TB-positive sample 3 | Positive |
| 13 | Clinical TB-positive sample 4 | Positive |
| 14 | Clinical TB-positive sample 5 | Positive |

1. Extracting DNA

To extract DNA from a serum sample, the following materials were used: Quick-cfDNA™ Serum & Plasma Kit (D4076) that contains S&P 5× Digestion Buffer, Proteinase K, S&P DNA Binding Buffer, Zymo-Spin™ III-S Column Assembly, S&P DNA Prep Wash Buffer, S&P DNA Wash Buffer, DNA Elution Buffer (10 nM Tris-HCL, pH 8.5, 0.1 mM EDTA), and 1.5 mL Tube.

If the serum sample is stored in −80° C., first place the sample at room temperature to thaw for 30 minutes. 100 µl of the thawed serum was mixed with 25 µl of S&P 5× Digestion Buffer and 10 µl of Proteinase K in a DNA Low Binding Tube.

Subsequently, the mixture was incubated at 55° C. for 30 minutes for digestion, followed by the addition of two volumes of S&P DNA Binding Buffer to the digested samples and mixed thoroughly.

The entire mixture was then transferred into Zymo-Spin™ III-S Column Assembly in a 1.5 ml tube, and centrifuged at 1000 g for 2 minutes. The flow-through was discarded.

400 µl of S&P DNA Prep Buffer was added to the column and centrifuged at ≥10000 g for 30 seconds, and the flow-through was discarded. The column was washed twice with 400 µl of S&P Wash Buffer, each centrifuged at ≥10000 g for 1 minute.

The column was then transferred into a 1.5 ml DNase-free tube. 40 µl of DNA Elution Buffer was added directly to the column matrix and incubated at room temperature for 3 minutes, followed by centrifugation at maximum speed for 30 seconds. The collected DNA was then stored at −20° C. until further use.

Additionally, to further increase the amount of cfDNA isolated, serum or plasma is preferably processed for less than 24 hours after blood draw to avoid DNA degradation. Whole blood can also be directly processed and used for the CRISPR detection discussed below. The blood correction tube can be EDTA-K or Na tube for plasma, or heparin for whole blood.

Figure 5:
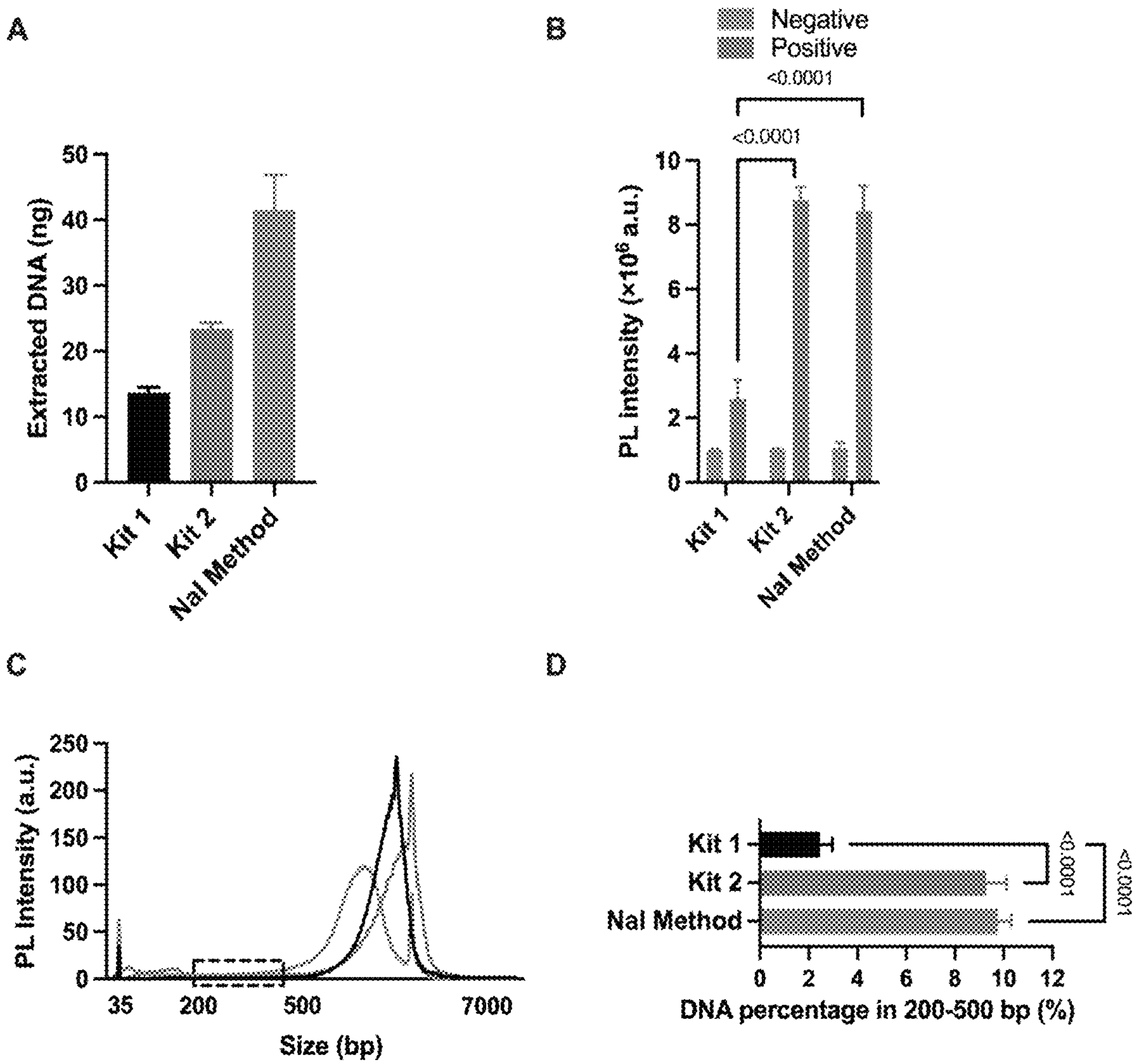
FIG. 5. Methods comparison to increase target DNA (200-500 bp cell free DNA) yield for CRISPR assay. A. Extracted DNA amount. B. CRISPR fluorescent intensity of TB IS6110 cell-free DNA. C. Extracted DNA size distribution measured by Bioanalyzer. D. Target DNA percentage in total extracted DNA.

The results of using Nal tube as compared to typical tubes are shown in FIG. 5. In FIG. 5(A), the amount of extracted DNA using the Nal method is approximately two times more than using Kit 1, and about 80% higher than Kit 2. In FIG. 5(B), the Nal-extracted DNA elicits fluorescent intensity similar to Kit 2. In FIG. 5(C), the extracted DNA size distribution using Nal method is consistent with Kits 1 & 2 in the 200 to 500 bp range, which is the target cfDNA size. In FIG. 5(D), the target DNA percentage using the Nal extraction method is similar to that of using Kit 2, and significantly higher than Kit 1. The target DNA percentage is defined as the percentage of 200-500 bp cfDNA among the total cfDNA, based on optical density of the gel image. These results indicate that Nal extraction method can further improve the amount of DNA isolated from the sample, while maintaining the same selectivity of target DNA.

2. Amplifying DNA

PCR was performed as an example of DNA amplification, and as discussed above, other DNA amplification techniques can be used. To perform PCR, the following materials were used: DEPC-Treated Water (1907041), Primer F and Primer R (List in the following table), 10× DNA Polymerase PCR Buffer, AccuPrime™ Taq DNA Polymerase System.

Three pairs of primers were designed to amplify IS6110, esxB and gryB of MTB genome. The reason for choosing IS6110, as discussed above, is because the MTB genome has multiple copies thereof that could increase sensitivity. Primers against esxB was designed because of esxB is conserved across different *Mycobacterium* species. Primers against gryB was designed specifically to detect whether the MTB is fluoroquinolone-resistant. The designed primers used in this step is listed below:

TABLE 2

PCR PRIMERS

| Target Gene | Name | Sequence (5'-3') |
|---|---|---|
| IS6110 | SEQ ID NO. 1 (F) | GGTCGGAAGCTCCTATGACAATGCACTAGCC |
| | SEQ ID NO. 2 (R) | TTGAGCGTAGTAGGCAGCCTCGAGTTCGAC |
| esxB | SEQ ID NO. 3 (F) | TAAAGAGAGAAAGTAGTCCAGCATGGCAGAG |
| | SEQ ID NO. 4 (R) | TCTCGTCGAGTTCCTGCTTCTGCTTATTGG |
| gryB | SEQ ID NO. 5 (F) | CTGTTGTTGACGTTGTTGTTCCGGTTCATGC |
| | SEQ ID NO. 6 (R) | CTGAATGCCGTCTTCCTTGTTGATCTTCTTC |

The following components were added to a sterile thin walled 0.2 ml PCR tube at room temperature:

| Components | Amount (μl) | Component | Amount (μl) |
|---|---|---|---|
| DEPC-treated water | 15.12 | Primer R | 0.4 |
| 10X DNA Polymerase PCR buffer with hybridization enhancer component | 2 | AccuPrime ™ Taq DNA Polymerase system | 0.08 |
| Primer F | 0.4 | Extracted DNA | 2 |

The content in the tubes was mixed well, and centrifuged briefly to collect the content. The tubes were incubated in a thermal cycler at 95° C. for 2 minutes to completely denature the DNA template and activate the enzyme.

35 cycles of PCR amplification were then performed as follows: denature: 95° C. for 30 seconds; anneal: 60° C. for 30 seconds; extend: 72° C. for 30 seconds. After completion of 35 cycles, the temperature of the reaction mixture was maintained at 4° C. The resulting PCR products was then stored at −20° C. until next step.

Additionally, more components may be added to the amplification buffer to increase the amplification efficiency. For example, blocker proteins of PCR/RPA inhibitory components, such as IgG, hemoglobin, lactoferrin etc., may be added to facilitate further amplification. Suitable blocker proteins may include rTth and Tli polymerases that are more resistant to DNA polymerase inhibitors present in clinical samples. Accessory proteins in the PCR/RPA buffers may also be added, such as BSA, DNA hybridization enhancers, and single-stranded DNA binding protein gp32. These accessory proteins can enhance specific primer-template hybridization during every cycle of PCR, preventing mis-priming and improving PCR specificity and yield.

rTth polymerase is derived from the *eubacterium Thermus thermophilus* HB8. It has proven to be more resistant to DNA polymerase inhibitors presented in clinical samples for DAN detection and also exhibits reverse transcriptase activity in the presence of $Mn^{2+}$ ions. Tli DNA polymerase (also known as Vent® DNA polymerase) was derived from the hyperthermophile *Thermococcus litoralis*, and it also shows high blood tolerance. Both these polymerases are suitable for direct blood sample amplification.

Additionally, bovine serum albumin (BSA) and T4 bacteriophage gene 32 product (gp32) are good candidates to inhibit proteinase in blood samples, as they are effective against iron chloride, hemin, fulminic acid, humic acid, tannic acid, stool extracts and melanin.

Figure 6:
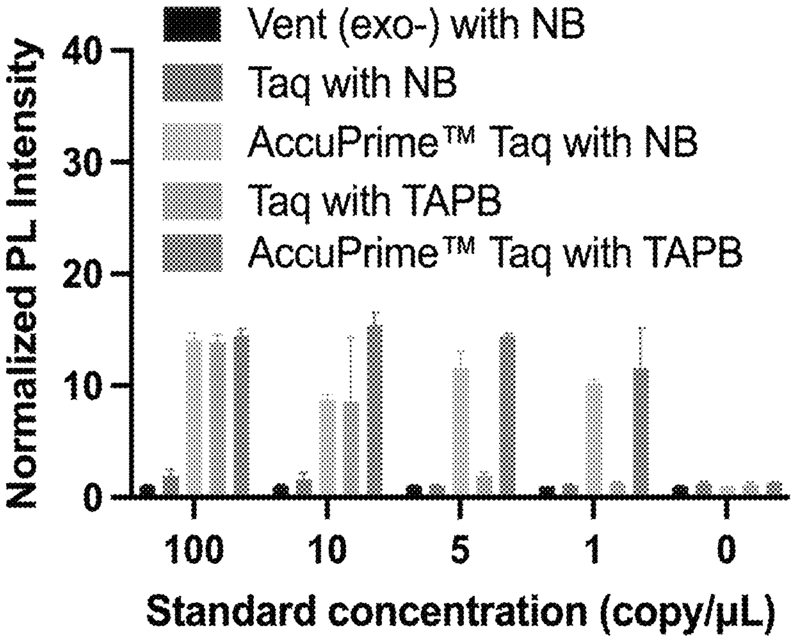
FIG. 6. Comparison of different DNA polymerases and accessory protein components in PCR/RPA buffer. NB: normal buffer reference; TAPB: normal buffer supplemented with thermostable AccuPrime protein reagent and 10% glycerol.

The results of adding accessory protein components with different DNA polymerase systems are shown in FIG. 6, in which NB stands for normal buffer reference, and TAPB stands for normal buffer supplemented with thermostable AccuPrime™ protein reagent and 10% glycerol. It is shown that when using AccuPrime™ Taq polymerase with TAPB (comprising the accessory proteins), the PI intensity are 5 to 10 times higher than Taq with NB or Vent® with NB. This shows that the accessory proteins are capable of improving the amplification efficiency.

3. Crispr Detection

After the amplification step, MTB detection with CRISPR-Cas system was performed with the following materials: DEPC-Treated Water (1907041), EnGen® Lba Cas12a (Cpf1), 10× NEBuffer™ 2.1, gRNA (list in the following table), Fluorescent Reporter (5'-6-FAM-TTTTTTTTTTTT-BHQ1), and Corning® 96 Well Half-Area Microplate.

As discussed above, the gRNA sequences were designed in accordance with the target fragments and PCR primers, and are listed below:

TABLE 3

| gRNA sequence | | |
|---|---|---|
| Target Gene | Name | Sequence (5'-3') |
| IS6110 | SEQ ID NO. 7 | UAAUUUCUACUCUUGUAGAUAUCAGCUCGGUCUUGAAUAG |
| esxB | SEQ ID NO. 8 | UAAUUUCUACUCUUGUAGAUGAGCGGAUCUCCGGCGACCU |
| gryB | SEQ ID NO. 9 | UAAUUUCUACUCUUGUAGAUGCACAACCGCCGCUGUACAA |

To carry out the CRISPR detection step, the following components were added to a Half-area Microplate well, mixed well and incubated at room temperature for 10 minutes:

| Components | Amount (μl) | Component | Amount (μl) |
|---|---|---|---|
| DEPC-treated water | 1.5 | 1 μM EnGen ® Lba Cas12a | 1 |
| 10X NEBuffer ™ 2.1 | 3 | 2 μM Fluorescent reporter | 1.5 |
| 300 nM gRNA | 3 | PCR product | 20 μL |

It is noted that the PCR product with the buffer solution mixture was added to the CRISPR detection mixture, as opposed to separating the PCR product from the buffer solution. This also increases the detection sensitivity.

Figure 2:
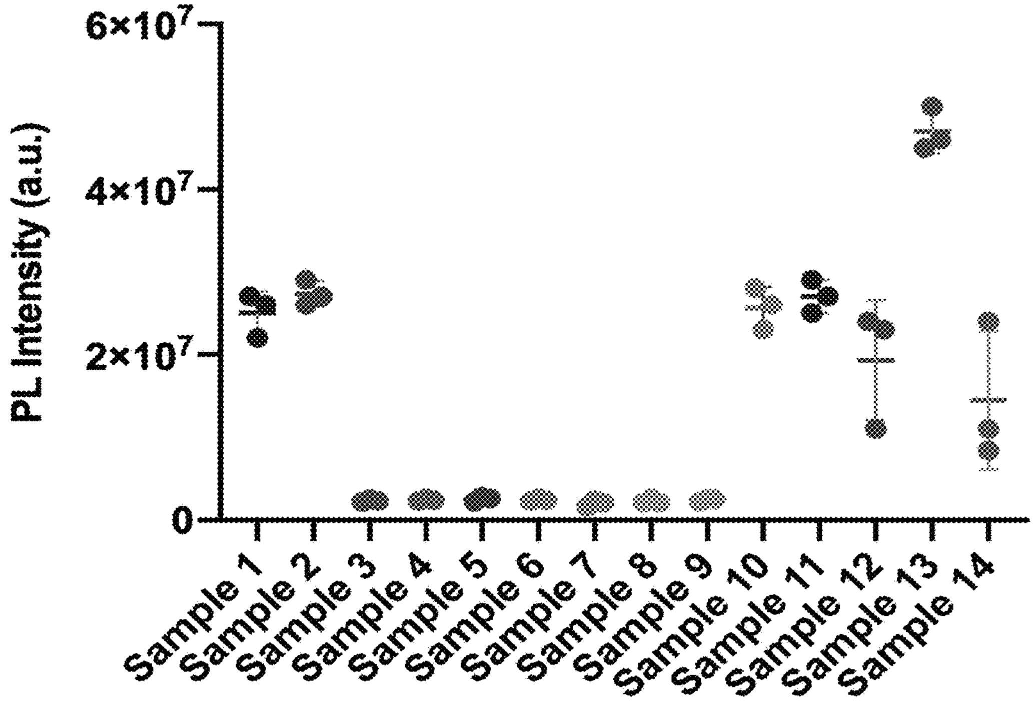
FIG. 2. Fluorescent results of the serum samples.

The system was incubated in the dark at 37° C. for 20 minutes with vibration. The fluorescent signal was measured with a plate reader. The result is shown in FIG. 2. When the sample produces signal intensity two times higher than that of the negative control, it is defined as positive. As can be seen in FIG. 2, positive samples 1, 2, and 4 show fluorescent intensity comparable to the positive control, whereas negative sample 3 shows fluorescent intensity comparable to the negative control.

Example 2: NTM Pathogens

Figure 3:
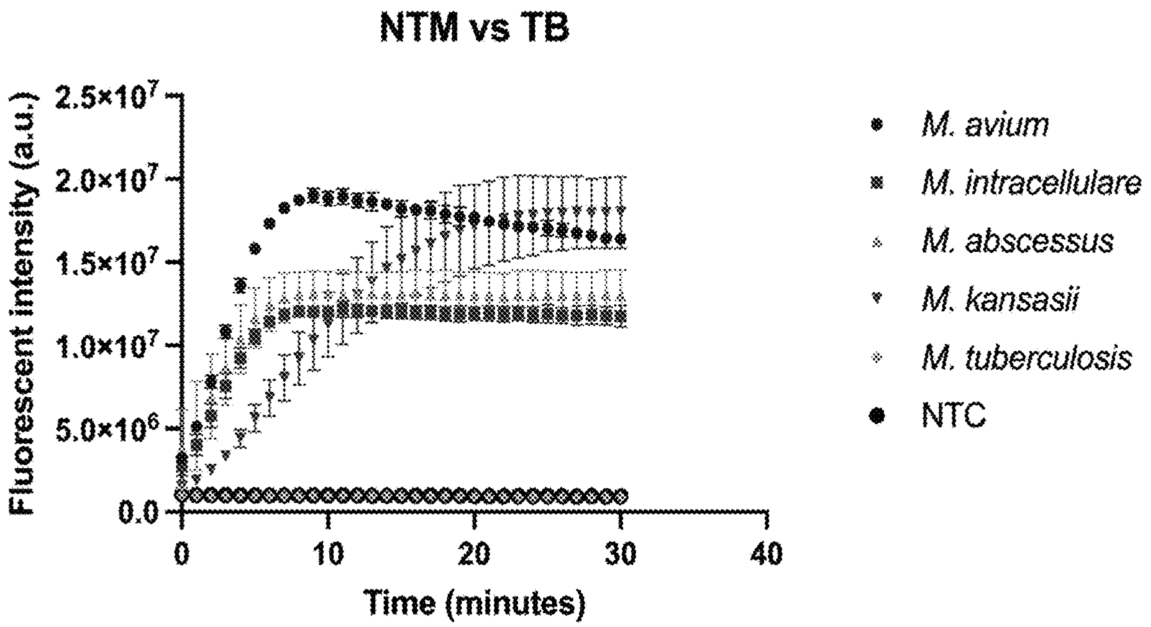
FIG. 3. NTM. targeting CRISPR assay.

To evaluate the applicability of the method on pathogens other than MTB, samples that contain various non-tuberculous mycobacteria were also collected and analyzed using the method described herein, except the gRNAs used were targeting different sequences. The results are shown in FIG. 3, which shows that *M. avium, M. intracellulare, M. abscessus, M. kansasii* can all be detected within similar timeframe as MTB. As such, the quick detection time is suitable for situations that require fast response time.

This proves that the method disclosed this in can be readily applied to other non-tuberculous mycobacteria, such as *M. simiae, M. marinum, M. scrofulaceum, M. szulgai., M. avium* complex (MAC), M. *ulcerans, M. xenopi, M. malmoense, M. terrae, M. haemophilum, M. genavense, M. chelonae, M. abscessus, M. fortuitum, M. peregrinum, M. smegmatis* and *M. flavescens.*

Example 3: Pathogens Other than Mycobacteria

Figure 4:
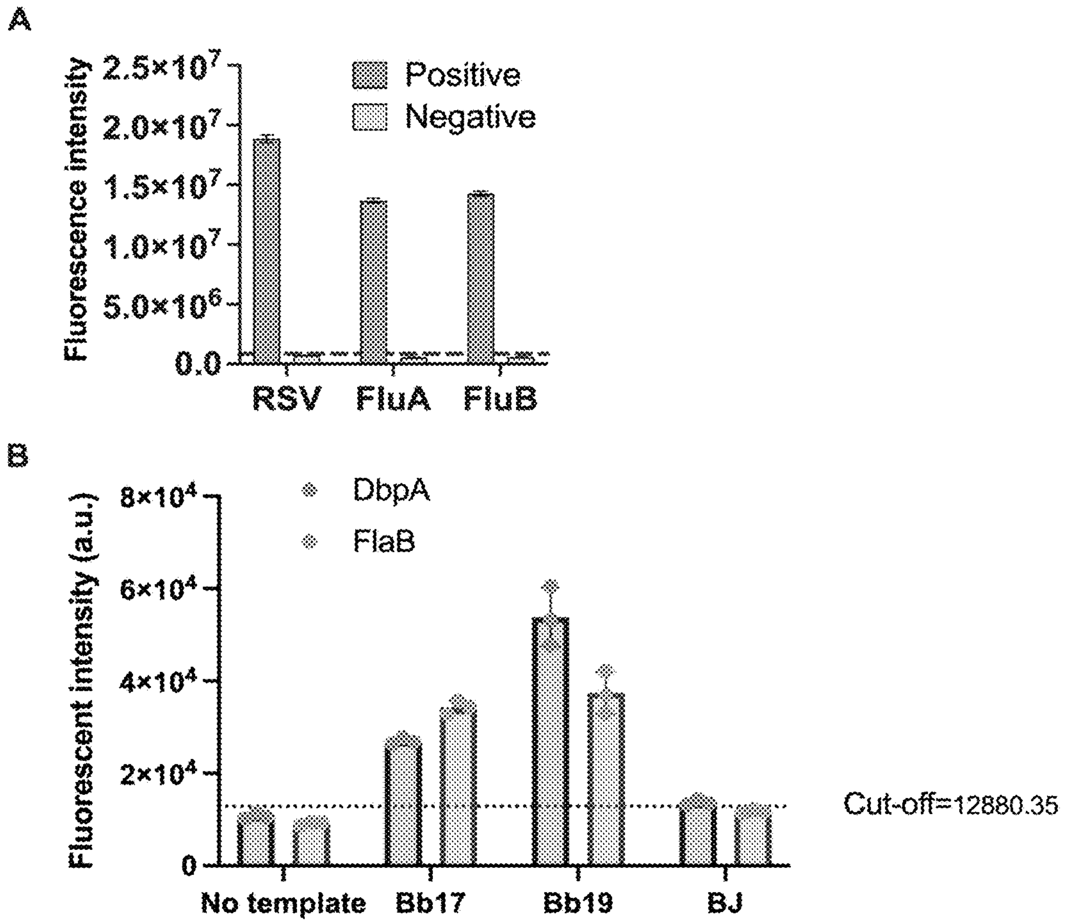
FIG. 4. Example of new pathogen detection with CRISPR assay. A CRISPR targeting RSV, FluA and FluB. B. CRISPR assay targeting Lyme desease pathogen (*Borrelia burgdorferi*) DbpA and FlaB gene.

To evaluate the applicability of the method on pathogens other than mycobacteria, samples that contain various pathogens were also collected and analyzed using the method described herein, except the gRNAs used were targeting different sequences. The results are shown in FIG. 4, which shows that RSV (respiratory syncytial virus), FluA, FluB and Lyme disease can all be detected with satisfactory. In (A), the positive results of all three viruses are significantly higher than negative ones for easy detection. In (B), both DbpA and FlaB gene show significantly higher fluorescence intensity in positive samples for positive detection.

This shows that the method disclosed herein can be readily applied to other viral pathogens, including but not limited to, Cytomegalovirus (CMV), Varicella-zoster virus (VZV), Ebola virus, Marburg virus, West Nile virus (WNV), Zika virus, yellow fever virus, Herpes simplex virus (HSV), Monkeypox virus, Lyme diseases (bacterium *Borrelia burgdorferi* and *Borrelia mayonii*), malaria (*Plasmodium falciparum* and *Plasmodium vivax*), *Pneumocystis* pneumonia (*Pneumocystis jirovecii*), Human Herpesvirus (HHV).

Prophetic Example 1

To obtain best results, the ratio of (Cas12a:gRNA:reporter molecule) in the CRISPR detection step is varied, otherwise the DNA extraction, DNA amplification and CRISPR detection steps are the same as Example 1. This optimized ratio will further improve the specificity and sensitivity of this method.

Prophetic Example 2

To further improve the sensitivity of this method, MTB-DNA enriching and/or human-DNA depletion from the serum sample will be performed prior to the DNA amplification step. Human DNA has a specific methylation pattern that serves as the epitope of anti-human DNA antibodies. By treating the extracted DNA with the anti-human DNA antibodies to deplete human DNA in the serum sample, it is expected to further improve the sensitivity of the method of this disclosure.

Similarly, MTB DNA has its own specific methylation patterns that are lineage- or species-specific, and can serve as epitopes for anti-MTB antibodies. Therefore, by treating the serum sample with anti-MTB antibodies to capture only MTB DNA fragments, the sensitivity of this method can be further improved.

The following references are incorporated by reference in their entirety for all purposes.

What is claimed is:

1. A method of detecting a pathogen in a bodily fluid sample, comprising the steps of:

a) amplifying a target nucleic acid sequence from a bodily fluid sample, wherein the target nucleic acid sequence is specific to the pathogen; and b) detecting presence of the target nucleic acid sequence using a CRISPR-mediated system, wherein the CRISPR-mediated system comprises a CRISPR effector protein, a guide RNA (gRNA) that hybridizes with a *Mycobacterium tuberculosis* (MTB) target nucleic acid fragment, wherein the gRNA is at least one of SEQ ID NOs. 7, 8 or 9, and a reporter molecule that is detectable on cleavage by the CRISPR effector protein.

2. The method of claim 1, wherein the pathogen is selected from: *M. tuberculous, M. kansasii, M. simiae, M. marinum, M. scrofulaceum, M. szulgai, M. avium* complex (MAC), *M. ulcerans, M. xenopi, M. malmoense, M. terrae, M. haemophilum, M. genavense, M. chelonae, M. abscessus, M. fortuitum, M. peregrinum, M. smegmatis, M. flavescens*, Respiratory syncytial virus (RSV), Cytomegalovirus (CMV), Varicella-zoster virus (VZV), Ebola virus, Marburg virus, West Nile virus (WNV), Zika virus, yellow fever virus, Herpes simplex virus (HSV), Monkeypox virus, Lyme diseases (bacterium *Borrelia burgdorferi* and *Borrelia* mayonii), malaria (*Plasmodium falciparum* and *Plasmodium \vivax*), *Pneumocystis* pneumonia (*Pneumocystis jirovecii*), and Human Herpesvirus (HHV).

3. The method of claim 1, further comprises, prior to step a), the following step:

a-1) extracting nucleic acids from the bodily fluid sample.

4. The method of claim 3, wherein the time between step a-1) and step a) is less than 24 hours.

5. The method of claim 1, wherein in step a) is performed in an amplification buffer, wherein the amplification buffer comprises nucleic acid polymerase, primers, and at least one of a blocker protein, a hybridization enhancer, and an accessory protein.

6. The method of claim 5, wherein the blocker protein is rTth or Tli.

7. The method of claim 5, wherein the accessory protein is bovine serum albumin (BSA), DNA hybridization enhancers, or T4 bacteriophage gene 32 product (gp32).

8. The method of claim 3, wherein in step a-1) the extracting step further comprising:

a-2) depleting human DNA using anti-human DNA antibodies.

9. The method of claim 3, further comprising the addition of proteinase K.

10. The method of claim 1, wherein step a) is carried out using polymerase chain reaction (PCR), recombinase polymerase amplification (RPA), nucleic acid sequence-based amplification (NASBA), rolling circle amplification (RCA), or loop-mediated isothermal amplification (LAMP).

11. The method of claim 10, wherein a hybridization enhancer is used in the PCR, and the hybridization enhancer is transferred into the detecting step b).

12. The method of claim 1, wherein in step b) the CRISPR effector protein is selected from Cas12a, Cas9 and/or Cas13.

13. The method of claim 1, wherein in step b) the CRISPR effector protein is selected from a group consisting of AsCas12a, FnCas12a, LbCas12a, AacCas12b, LwaCas13a, AapCas12b, Un1Cas14a1, BbCas12a, HkCas12a, OsCas12a, BoCas12a, TsCas12a.

14. The method of claim 1, wherein the reporter molecule is a single-stranded DNA or a single-stranded RNA labeled with fluorescence and quencher, gold nanoparticles, or biotin-FAM.

15. The method of claim 1, wherein the bodily fluid sample is obtained from serum, plasma, saliva, or urine.

16. The method of claim 2, wherein the target DNA sequence is a portion of IS6110, IS986, esxB, gryB, rpoB, katG, inhA, rpsL, rrs, gyrA, gyrB, embB, eis and pncA.

17. The method of claim 1, wherein a pair of primers are used in step b) for the DNA amplification, wherein the primers are SEQ ID NOs. 1 and 2, SEQ ID NOs. 3 and 4, or SEQ ID NOs. 5 and 6.

* * * * *

SEQUENCE LISTING

```
Sequence total quantity: 9
SEQ ID NO: 1           moltype = DNA  length = 31
FEATURE                Location/Qualifiers
misc_feature           1..31
                       note = Synthesized PCR primer
source                 1..31
                       mol_type = other DNA
                       organism = synthetic construct
SEQUENCE: 1
ggtcggaagc tcctatgaca atgcactagc c                                 31

SEQ ID NO: 2           moltype = DNA  length = 30
FEATURE                Location/Qualifiers
misc_feature           1..30
                       note = Synthesized PCR primer
source                 1..30
                       mol_type = other DNA
                       organism = synthetic construct
SEQUENCE: 2
ttgagcgtag taggcagcct cgagttcgac                                   30

SEQ ID NO: 3           moltype = DNA  length = 31
FEATURE                Location/Qualifiers
misc_feature           1..31
                       note = Synthesized PCR primer
source                 1..31
                       mol_type = other DNA
                       organism = synthetic construct
SEQUENCE: 3
taaagagaga aagtagtcca gcatggcaga g                                 31

SEQ ID NO: 4           moltype = DNA  length = 30
FEATURE                Location/Qualifiers
misc_feature           1..30
                       note = Synthesized PCR primer
source                 1..30
                       mol_type = other DNA
                       organism = synthetic construct
SEQUENCE: 4
tctcgtcgag ttcctgcttc tgcttattgg                                   30

SEQ ID NO: 5           moltype = DNA  length = 31
FEATURE                Location/Qualifiers
misc_feature           1..31
                       note = Synthesized PCR primer
source                 1..31
                       mol_type = other DNA
                       organism = synthetic construct
SEQUENCE: 5
ctgttgttga cgttgttgtt ccggttcatg c                                 31

SEQ ID NO: 6           moltype = DNA  length = 31
FEATURE                Location/Qualifiers
misc_feature           1..31
                       note = Synthesized PCR primer
source                 1..31
                       mol_type = other DNA
                       organism = synthetic construct
SEQUENCE: 6
ctgaatgccg tcttccttgt tgatcttctt c                                 31

SEQ ID NO: 7           moltype = RNA  length = 40
FEATURE                Location/Qualifiers
misc_feature           1..40
                       note = Synthesized PCR primer
source                 1..40
                       mol_type = other RNA
                       organism = synthetic construct
SEQUENCE: 7
taatttctac tcttgtagat atcagctcgg tcttgaatag                        40

SEQ ID NO: 8           moltype = RNA  length = 40
FEATURE                Location/Qualifiers
misc_feature           1..40
                       note = Synthesized PCR primer
source                 1..40
                       mol_type = other RNA
                       organism = synthetic construct
```

-continued

```
SEQUENCE: 8
taatttctac tcttgtagat gagcggatct ccggcgacct                      40

SEQ ID NO: 9             moltype = RNA  length = 40
FEATURE                  Location/Qualifiers
misc_feature             1..40
                         note = Synthesized PCR primer
source                   1..40
                         mol_type = other RNA
                         organism = synthetic construct
SEQUENCE: 9
taatttctac tcttgtagat gcacaaccgc cgctgtacaa                      40
```